United States Patent
Paul et al.

(10) Patent No.: US 10,539,641 B2
(45) Date of Patent: Jan. 21, 2020

(54) ATTENUATION MAP FOR COMBINED MAGNETIC RESONANCE/POSITRON EMISSION TOMOGRAPHY IMAGING

(71) Applicant: Siemens Healthcare GmbH, Erlangen (DE)

(72) Inventors: Dominik Paul, Bubenreuth (DE); Mario Zeller, Erlangen (DE); Flavio Carinci, Wurenlingen (CH)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/412,713

(22) Filed: May 15, 2019

(65) Prior Publication Data
US 2019/0361085 A1 Nov. 28, 2019

(30) Foreign Application Priority Data
May 24, 2018 (DE) .................. 10 2018 208 202

(51) Int. Cl.
*G01R 33/565* (2006.01)
*G01R 33/48* (2006.01)
(Continued)

(52) U.S. Cl.
CPC ...... *G01R 33/56563* (2013.01); *A61B 5/0035* (2013.01); *A61B 5/055* (2013.01);
(Continued)

(58) Field of Classification Search
CPC ............ G01R 33/56563; G01R 33/481; G01R 33/56572; A61B 5/0035; A61B 5/055; A61B 6/037; A61B 6/5247
See application file for complete search history.

(56) References Cited

U.S. PATENT DOCUMENTS

2011/0187364 A1 8/2011 Blumhagen et al.
2013/0237806 A1 9/2013 Blumhagen et al.
(Continued)

FOREIGN PATENT DOCUMENTS

DE 102010006431 A1 8/2011
DE 102012203782 A1 9/2013
(Continued)

OTHER PUBLICATIONS

German Office Action (TB 100a/12.54) for German Application No. DE102018208202.2 dated Mar. 15, 2019. (German).
(Continued)

*Primary Examiner* — Michael T Rozanski
(74) *Attorney, Agent, or Firm* — Harness, Dickey & Pierce, P.L.C.

(57) ABSTRACT

A method is for providing an attenuation map of a patient, suitable for correcting PET data of the patient acquired with combined magnetic resonance/positron emission tomography imaging in a magnetic resonance/positron emission tomography system. In an embodiment, the method includes acquiring magnetic resonance data with at least one imaging scan in the magnetic resonance/positron emission tomography system; determining the attenuation map of the patient using the magnetic resonance data and providing the attenuation map of the patient for correcting the PET data of the patient acquired with combined magnetic resonance/positron emission tomography imaging.

20 Claims, 7 Drawing Sheets

(51) Int. Cl.
    *A61B 5/00*          (2006.01)
    *A61B 5/055*        (2006.01)
    *A61B 6/03*          (2006.01)
    *A61B 6/00*          (2006.01)

(52) U.S. Cl.
    CPC ............ *A61B 6/037* (2013.01); *A61B 6/5247* (2013.01); *G01R 33/481* (2013.01); *G01R 33/56572* (2013.01)

(56) References Cited

U.S. PATENT DOCUMENTS

| | | |
|---|---|---|
| 2014/0009153 A1 | 1/2014 | Blumhagen et al. |
| 2015/0196266 A1 | 7/2015 | Fenchel |

FOREIGN PATENT DOCUMENTS

| | | |
|---|---|---|
| DE | 102012211471 A1 | 1/2014 |
| DE | 102014200303 A1 | 7/2015 |

OTHER PUBLICATIONS

German Office Action (TB 100a/12.54) for German Application No. DE102018208202.2 dated Mar. 15, 2019. (English).

Decision to Grant a Patent for German Application No. DE102018208202.2 dated Apr. 10, 2019. (German).

Decision to Grant a Patent for German Application No. DE102018208202.2 dated Apr. 10, 2019. (English).

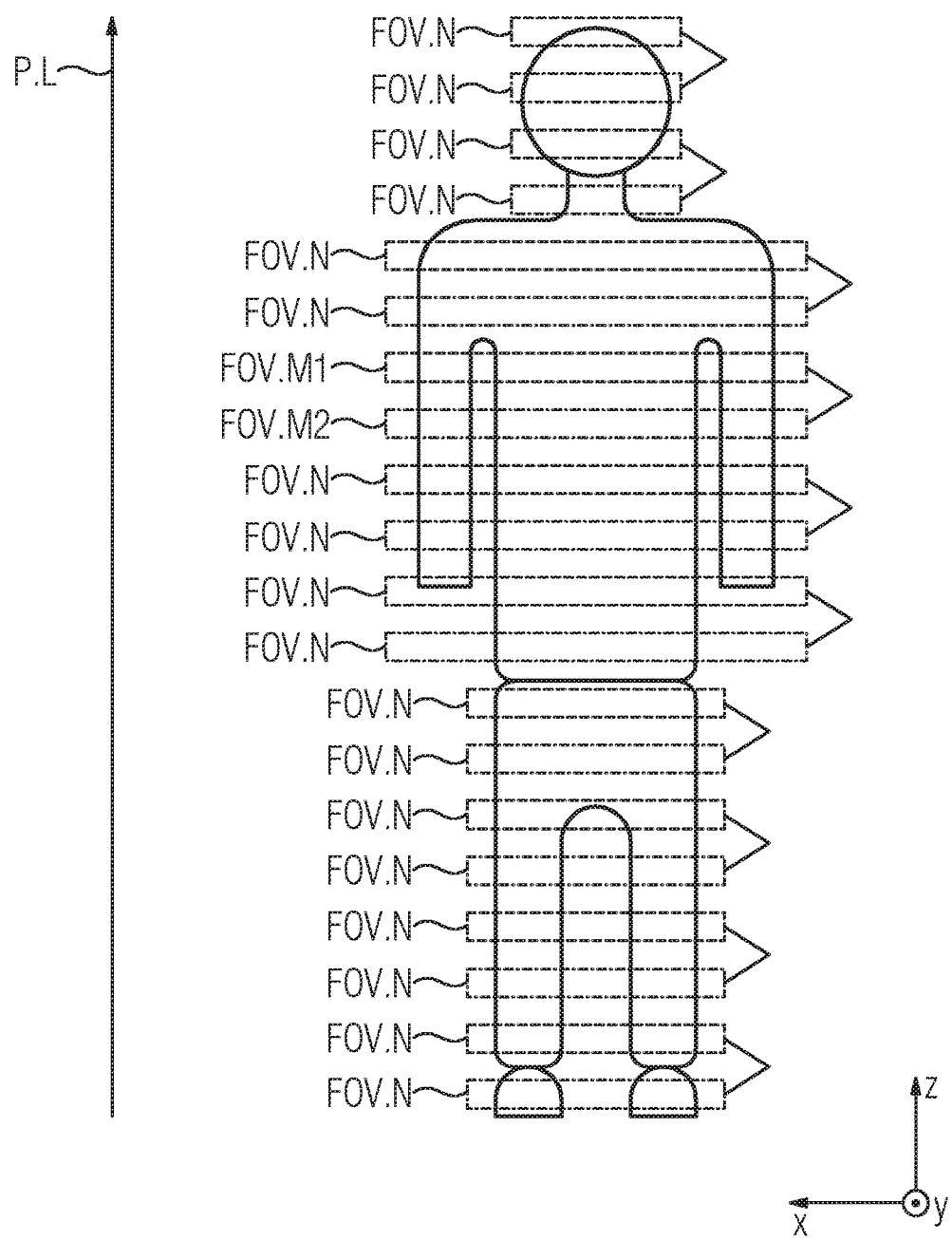

ATTENUATION MAP FOR COMBINED MAGNETIC RESONANCE/POSITRON EMISSION TOMOGRAPHY IMAGING

PRIORITY STATEMENT

The present application hereby claims priority under 35 U.S.C. § 119 to German patent application number DE 102018208202.2 filed May 24, 2018, the entire contents of which are hereby incorporated herein by reference.

FIELD

Embodiments of the invention generally relate to a method for providing an attenuation map of a patient, a method for providing corrected PET data of the patient acquired with combined magnetic resonance/positron emission tomography imaging in a magnetic resonance/positron emission tomography system, the magnetic resonance/positron emission tomography system and an associated computer program product.

BACKGROUND

An attenuation map is usually created with combined magnetic resonance/positron emission tomography imaging (MRI-PET imaging) in a magnetic resonance/positron emission tomography system (MRI-PET system). The MRI-PET system typically includes a magnetic resonance imaging scanner (MRI) and a positron emission tomography scanner (PET). MRI-PET imaging typically includes at least one MRI imaging scan (MRI imaging) and at least one PET imaging scan (PET imaging).

The attenuation map can be determined based on magnetic resonance data (MRI data), which is preferably acquired with MRI imaging. Positron emission data (PET data) acquired with PET imaging is usually corrected by way of the attenuation map. Typically, in MRI, a maximum field of view, in which the MRI data can be acquired in principle, is limited in all three spatial directions due to physical and/or technical restrictions. Such restrictions are usually non-linearity of an MRI magnetic gradient field and/or localized homogeneity of an MRI main magnetic field, which can result in B0 field inhomogeneities.

For this reason, typically a scan region of the MRI imaging is limited to a region within the maximum field of view in which the aforementioned restrictions are preferably within specific limit values thereby usually enabling substantially distortion-free MRI imaging. During MRI imaging, distortion typically occurs outside the maximum field of view in a peripheral region of the MRI as a result of which the image quality of magnetic resonance images (MRI images) reconstructed using the MRI data can be impaired. In particular in this context, distortion means that a signal value at a predetermined location of an examination object appears at another location in the MRI images of the examination object.

MRI-PET imaging typically requires the scan region to fill the maximum field of view, wherein the maximum field of view is preferably defined as broadly as possible. This is because, if the examination object is a patient, the patient's extremities, in particular the arms, are located in a peripheral region in which the aforementioned restrictions are typically outside the specific limit values. Nevertheless, the attenuation map is typically determined for an entire body of a patient, including the arms. If the arms are located in the peripheral region the MRI data may have deviating signal values as a result. However, usually even a slight deviation in the MRI data is serious with respect to the determination of the attenuation map because there is typically an exponential dependence between attenuation values within the attenuation map and the MRI data.

DE 10 2010 006 431 A1 describes a method for determining a location of a subarea of an examination object in a magnetic resonance system, wherein the subarea is arranged at the edge of a field of view of the magnetic resonance system, wherein at least one slice position is determined for an MR image in which the B0 field at the edge of the MR image satisfies a predetermined homogeneity criterion, wherein an MR image is acquired in the specific slice position, wherein the MR image contains the subarea at the edge of the field of view and wherein the location of the subarea of the examination object is determined by the location of the subarea in the MR image.

A method disclosed in DE 10 2012 203 782 A1 describes a further possibility for avoiding the aforementioned restrictions. DE 10 2012 203 782 A1 discloses a method for performing combined magnetic resonance/positron emission tomography imaging of an examination object in a MR-PET system with which inter alia magnetic resonance data is acquired using a first readout gradient field, wherein the first readout gradient field is selected such that, at a predetermined location of the field of view of the magnetic resonance system, distortion caused by non-linearity of the first readout gradient field and distortion caused by B0 field inhomogeneity substantially cancel each other out.

Typically, such a method requires the readout gradient field to be adapted separately for two sides of the scan region, for example the sides with the two arms of the patient. Therefore, typically, there are two imaging scans wherein initially a first side of the patient is acquired and subsequently a second side of the patient is acquired. For these two MRI imaging scans, typically an amplitude of the readout gradient field is set independently for each side and one scan taken in the head-foot direction and another in the foot-head direction. Therefore, the two MRI imaging scans can require a patient bench bearing the patient to be moved to-and-fro, thereby prolonging the overall scan time.

Furthermore, sequence parameters of the two MRI imaging scans are not usually specifically adapted to the patient, in particular to the location and/or anatomy of the patient. In other words, typically the sequence parameters of the MRI imaging scans are defined independently of whether a, and/or which, patient is located on the patient bench.

SUMMARY

Embodiments of the invention are directed to a method for providing an attenuation map of a patient, a method for providing corrected PET data of the patient acquired with combined magnetic resonance/positron emission tomography imaging in a magnetic resonance/positron emission tomography system, the magnetic resonance/positron emission tomography system and an associated computer program product with which the provision of the attenuation map is improved.

Advantageous embodiments are described in the claims.

The method according to an embodiment of the invention for providing an attenuation map of a patient, which is suitable for correcting PET data of the patient acquired with combined magnetic resonance/positron emission tomography imaging in a magnetic resonance/positron emission tomography system includes:

acquiring magnetic resonance data with at least one imaging scan in the magnetic resonance/positron emission tomography system, determining the attenuation map of the patient using the magnetic resonance data and providing the attenuation map of the patient for correcting the PET data of the patient acquired with combined magnetic resonance/positron emission tomography imaging, wherein the acquiring of the magnetic resonance data includes:

acquiring first items of projection data of the patient in a substantially axial direction of the patient, acquiring second items of projection data of the patient in the substantially axial direction of the patient, determining third items of projection data by merging the first items of projection data of the patient and the second items of projection data of the patient, determining the mapping of the patient using the third items of projection data, adaptation of at least one sequence parameter of the at least one imaging scan in accordance with the mapping of the patient and performance of the at least one imaging scan, wherein the magnetic resonance data is acquired.

The method according to at least one embodiment of the invention for providing corrected PET data of the patient acquired with combined magnetic resonance/positron emission tomography imaging in a magnetic resonance/positron emission tomography system includes:

acquiring the PET data of the patient in the magnetic resonance/positron emission tomography system, providing the attenuation map, correcting the PET data of the patient using the attenuation map and providing the corrected PET data of the patient.

The magnetic resonance/positron emission tomography system according to at least one embodiment of the invention includes a magnetic resonance imaging scanner. The magnetic resonance imaging scanner is advantageously embodied to perform the method for providing the attenuation map of the patient, which is suitable for correcting the PET data of the patient acquired with combined magnetic resonance/positron emission tomography imaging in the magnetic resonance/positron emission tomography system, and its embodiments and therefore also includes the above-described advantages.

One embodiment provides that the magnetic resonance/positron emission tomography system includes a positron emission tomography scanner. The MRI-PET system is preferably embodied to perform the method for providing the corrected PET data of the patient acquired with combined magnetic resonance/positron emission tomography imaging and its embodiments and therefore also includes the above-described advantages.

The computer program product according to at least one embodiment of the invention includes program code modules/segments, which can be loaded into a computing unit of the magnetic resonance/positron emission tomography system to carry out a method according to the invention when the program code modules/segments are executed in the computing unit.

The computer program product can be a computer program or comprise a computer program. The computer program product in particular includes program code modules/segments that map the method steps according to at least one embodiment of the invention. This enables the method according to at least one embodiment of the invention to be carried out in a defined and repeatable manner and control to be exercised over the forwarding of the method according to at least one embodiment of the invention. The computer program product is preferably configured such that the computing unit can carry out the method steps according to at least one embodiment of the invention by way of the computer program product.

The program code segments/modules can in particular be loaded into a memory of the computing unit and typically executed via a processor of the computing unit with access to the memory. When the computer program product, in particular the program code segments/modules, is executed in the computing unit, typically all the inventive embodiments of the described method can be performed.

The computer program product is, for example, stored on a physical computer-readable medium and/or held digitally as a data packet in a computer network. The computer program product can represent the physical computer-readable medium and/or the data packet in the computer network. Thus, at least one embodiment of the invention can also be based on the physical computer-readable medium and/or the data packet in the computer network. The physical computer-readable medium can usually be connected directly to the computing unit, for example in that the physical, computer-readable medium is inserted into a DVD drive or plugged into a USB port as a result of which the computing unit is able to access, in particular read, the physical computer-readable medium.

BRIEF DESCRIPTION OF THE DRAWINGS

The following describes and explains the invention in more detail with reference to the example embodiments depicted in the figures. In principle, in the following description of the figures, structures and units that are substantially the same are given the same reference characters as on the first occurrence of the respective structure or unit.

The figures show.

DETAILED DESCRIPTION OF THE EXAMPLE EMBODIMENTS

Figure 1:
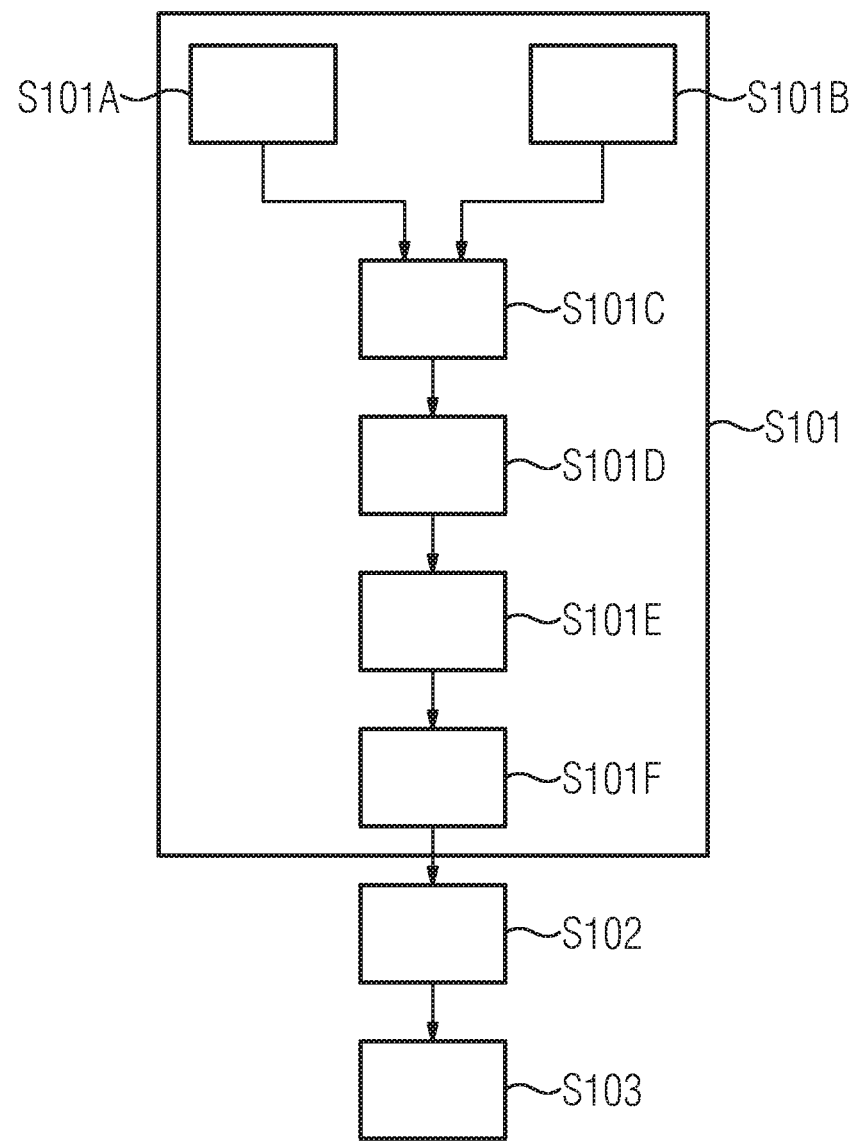
FIG. 1 a flow diagram of a method for providing an attenuation map of a patient in a first example embodiment, FIG. 2 a schematic view of a magnetic resonance/positron emission tomography system in a second example embodiment, FIG. 3 a flow diagram of a method for providing corrected PET data of the patient acquired with combined magnetic resonance/positron emission tomography imaging in a magnetic resonance/positron emission tomography system in a third example embodiment, FIG. 4 a flow diagram of a method for providing an attenuation map of a patient in a fourth example embodiment, FIG. 5 possible positioning of a scan region of the first items of projection data, a scan region of the second items of projection data and a scan region of the at least one imaging scan, FIG. 6 an illustrative sequence diagram with example data and FIG. 7 possible positioning of possible partial scan regions of a plurality of partial scans.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules.

Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

The method according to an embodiment of the invention for providing an attenuation map of a patient, which is suitable for correcting PET data of the patient acquired with combined magnetic resonance/positron emission tomography imaging in a magnetic resonance/positron emission tomography system includes:

acquiring magnetic resonance data with at least one imaging scan in the magnetic resonance/positron emission tomography system, determining the attenuation map of the patient using the magnetic resonance data and providing the attenuation map of the patient for correcting the PET data of the patient acquired with combined magnetic resonance/positron emission tomography imaging, wherein the acquiring of the magnetic resonance data includes:

acquiring first items of projection data of the patient in a substantially axial direction of the patient, acquiring second items of projection data of the patient in the substantially axial direction of the patient, determining third items of projection data by merging the first items of projection data of the patient and the second items of projection data of the patient, determining the mapping of the patient using the third items of projection data, adaptation of at least one sequence parameter of the at least one imaging scan in accordance with the mapping of the patient and performance of the at least one imaging scan, wherein the magnetic resonance data is acquired.

The method according to at least one embodiment of the invention in particular may have at least one of the following advantages:

The attenuation map of the patient is preferably provided more quickly because the acquisition of the magnetic resonance data (MRI data) is adapted specifically for the patient. In other words, the acquisition of the MRI data can be performed more quickly in that the at least one sequence parameter is advantageously adapted in accordance with the mapping of the patient. Usually, the result of this adaptation is that an extent of the scan region is defined in accordance with the mapping of the patient as a result of which the image quality of magnetic resonance images (MRI images) reconstructed using the MRI data can preferably be enhanced.

A possible further advantage is that, due to the patient-specific adaptation, the attenuation map has a higher quality than when a conventional attenuation map is acquired without reference to a specific patient.

One embodiment provides that the adaptation of the at least one sequence parameter includes a definition of a readout gradient field of the at least one imaging scan in accordance with the mapping of the patient in that, at a predetermined location within a scan region of the at least one imaging scan, distortion caused by non-linearity of the readout gradient field and distortion caused by B0 field inhomogeneity substantially cancel each other out. Advantageously, this can enhance the quality of the attenuation map because the distortion is reduced as a result of which typically the determination of the attenuation map is positively influenced as a result of an exponential dependence between attenuation values within the attenuation map and the MRI data.

One embodiment provides that the mapping of the patient includes a maximum axial extent of the patient. In this case, the attenuation map can be provided patient-specifically taking account of the anatomy and/or location of the patient. In other words, in this embodiment, the at least one sequence parameter is advantageously adapted to the anatomy and/or location of the patient.

One embodiment provides that the adaptation of the at least one sequence parameter includes a definition of a substantially axial extent of a scan region of the at least one imaging scan in accordance with the mapping of the patient. According to this embodiment, the scan region can be adapted to the patient such that the scan region advantageously maps the region of a body of the patient, which ideally should be included in the attenuation map for combined magnetic resonance/positron emission tomography imaging (MRI-PET imaging) so that the PET data acquired with MRI-PET imaging can in particular be corrected for the entire body of the patient. A further advantage can be that the scan region does not map any other region outside the body of the patient. In this case, preferably the entire duration of the scan is reduced. This is because the greater the maximum axial extent of the patient, the longer the entire duration of the scan.

One embodiment provides that the adaptation of the at least one sequence parameter includes the division of the at least one imaging scan into a plurality of partial scans in accordance with the mapping of the patient. In this case, the quality of the attenuation map is preferably enhanced in that the plurality of partial scans in accordance with the mapping of the patient is optimally parameterized and/or items of scan data from the optimally parametrized partial scans are combined to form the magnetic resonance data (MRI data).

One embodiment provides that a plurality of scan regions is assigned to the plurality of partial scans and that the plurality of scan regions is arranged offset along a longitudinal axis of the patient. Advantageously, according to this embodiment, a patient bench, which typically bears the patient, can be moved during the at least one imaging scan. The entire duration of the scan can be reduced if the patient bench is moved during the at least one imaging scan. This is in particular advantageous because this enhances patient comfort and/or enables the performance of more imaging scans per unit of time. A further advantage of this embodiment can be that the axial extents of the plurality of scan regions can be set independently of one another due to the offset arrangement. As a result, it is preferably possible to reduce and/or prevent signal extinction during the performance of the plurality of partial scans in the plurality of scan regions.

One embodiment provides that the plurality of partial scans includes a first partial scan and a second partial scan, wherein during the performance of the first partial scan of the at least one imaging scan, first items of scan data are acquired, wherein during the performance of the second partial scan of the at least one imaging scan, second items of scan data are acquired and wherein the first items of scan data and/or the second items of scan data are displaced along the longitudinal axis of the patient such that the scan region of the first items of scan data and the scan region of the second items of scan data have the same longitudinal position along the longitudinal axis as a result of which the magnetic resonance data has the same longitudinal position. This embodiment is in particular advantageous, because typically signal extinction can be reduced and/or prevented during the performance of the plurality of partial scans in the plurality of scan regions and simultaneously the magnetic resonance data is not distributed along the longitudinal axis.

One embodiment provides that a scan region of the first items of projection data and a scan region of the second items of projection data are arranged offset along a longitudinal axis of the patient. Advantageously, the patient bench can in particular be moved during the acquisition of the first items of projection data and/or the acquisition of the second items of projection data. In this embodiment, signal extinction in the scan region of the first items of projection data and in the scan region of the second items of projection data is preferably reduced and/or prevented.

One embodiment provides that the first items of projection data of the patient and/or the second items of projection data of the patient are displaced along the longitudinal axis of the patient such that the first items of projection data and the second items of projection data along the longitudinal axis have the same longitudinal position as a result of which the third items of projection data of the patient have the same longitudinal position. This embodiment is advantageous in that the mapping of the patient typically has the same longitudinal position. In other words, in the third items of projection data, the patient is preferably mapped along a straight line.

One embodiment provides that, during the determination of the third items of projection data, the first items of projection data of the patient and the second items of projection data of the patient are merged such that the third items of projection data have an axial extent that is greater than an axial extent of the first items of projection data of the patient or than an axial extent of the second items of projection data of the patient. The first items of projection data and/or the second items of projection data can preferably acquire the entire body of the patient, in particular the arms of the patient with high image quality. Advantageously, the mapping can be determined more precisely using the third items of projection data because the first items of projection data and second items of projection data on which the third items of projection data are based have higher image quality than when conventional mapping with items of projection data that only map the entire body of the patient is determined. In other words, this embodiment has the advantage that the at least one imaging scan is divided into a plurality of optimal parameterized partial scans thereby enabling preferably distortion-free MRI imaging.

The method according to at least one embodiment of the invention for providing corrected PET data of the patient acquired with combined magnetic resonance/positron emission tomography imaging in a magnetic resonance/positron emission tomography system includes:

acquiring the PET data of the patient in the magnetic resonance/positron emission tomography system, providing the attenuation map, correcting the PET data of the patient using the attenuation map and providing the corrected PET data of the patient.

At least one embodiment has the advantage that the PET data with the attenuation map can be corrected more precisely because the attenuation map is determined by way of patient-specifically adapted MRI imaging. Furthermore, the corrected PET data can be provided more quickly because the patient-specifically adapted MRI imaging enables the attenuation map to be calculated more quickly.

The magnetic resonance/positron emission tomography system according to at least one embodiment of the invention includes a magnetic resonance imaging scanner. The magnetic resonance imaging scanner is advantageously embodied to perform the method for providing the attenuation map of the patient, which is suitable for correcting the PET data of the patient acquired with combined magnetic resonance/positron emission tomography imaging in the magnetic resonance/positron emission tomography system, and its embodiments and therefore also includes the above-described advantages.

One embodiment provides that the magnetic resonance/positron emission tomography system includes a positron emission tomography scanner. The MRI-PET system is preferably embodied to perform the method for providing the corrected PET data of the patient acquired with combined magnetic resonance/positron emission tomography imaging and its embodiments and therefore also includes the above-described advantages.

The computer program product according to at least one embodiment of the invention includes program code modules/segments, which can be loaded into a computing unit of the magnetic resonance/positron emission tomography system to carry out a method according to the invention when the program code modules/segments are executed in the computing unit.

The computer program product can be a computer program or comprise a computer program. The computer program product in particular includes program code modules/segments that map the method steps according to at least one embodiment of the invention. This enables the method according to at least one embodiment of the invention to be carried out in a defined and repeatable manner and control to be exercised over the forwarding of the method according to at least one embodiment of the invention. The computer program product is preferably configured such that the computing unit can carry out the method steps according to at least one embodiment of the invention by way of the computer program product.

The program code segments/modules can in particular be loaded into a memory of the computing unit and typically executed via a processor of the computing unit with access to the memory. When the computer program product, in particular the program code segments/modules, is executed in the computing unit, typically all the inventive embodiments of the described method can be performed.

The computer program product is, for example, stored on a physical computer-readable medium and/or held digitally as a data packet in a computer network. The computer program product can represent the physical computer-readable medium and/or the data packet in the computer network. Thus, at least one embodiment of the invention can also be based on the physical computer-readable medium and/or the data packet in the computer network. The physical computer-readable medium can usually be connected directly to the computing unit, for example in that the physical, computer-readable medium is inserted into a DVD drive or plugged into a USB port as a result of which the computing unit is able to access, in particular read, the physical computer-readable medium.

The data packet can preferably be retrieved from the computer network. The computer network can comprise the computing unit or be connected directly to the computing unit by way of a wide area network (WAN) or a (wireless) local area network connection (WLAN or LAN). For example, the computer program product can be held digitally on a cloud server at a storage location of the computer network and transferred by way of the WAN via the internet and/or by way of the WLAN or LAN to the computing unit in particular by retrieving a download link indicating the storage location of the computer program product.

Features, advantages or alternative embodiments of the invention mentioned in the description of the device can also be transferred to the method and vice versa. In other words, method claims can be developed with device claims and vice versa. In particular, the device according to embodiments of the invention can be used in the method.

FIG. 1 is a flow diagram of a method for providing an attenuation map of a patient P, which is suitable for correcting PET data of the patient acquired with combined magnetic resonance/positron emission tomography imaging (MRI-PET imaging) in a magnetic resonance/positron emission tomography system (MRI-PET system) 10, in a first example embodiment.

Method step S101 characterizes the acquisition of magnetic resonance data with at least one imaging scan in the magnetic resonance/positron emission tomography system 10.

Method step S101A characterizes the acquisition of first items of projection data of the patient P in a substantially axial direction of the patient P.

Method step S101B characterizes the acquisition of second items of projection data of the patient P in the substantially axial direction of the patient P.

Method step S101C characterizes the determination of third items of projection data by merging the first items of projection data of the patient P and the second items of projection data of the patient P.

Method step S101D characterizes the determination of mapping of the patient P using the third items of projection data.

Method step S101E characterizes the adaptation of at least one sequence parameter of the at least one imaging scan in accordance with the mapping of the patient P.

Method step S101F characterizes the performance of the at least one imaging scan, wherein the magnetic resonance data is acquired.

Method step S102 characterizes the determination of the attenuation map of the patient P using the magnetic resonance data.

Method step S103 characterizes the provision of the attenuation map of the patient P for correcting the PET data of the patient acquired with combined magnetic resonance/positron emission tomography imaging.

The acquisition of the magnetic resonance data (MRI data) can include the performance of the at least one imaging scan according to the at least one sequence parameter. The MRI data can be present as k-space data and/or as image-space data. The k-space data is typically raw data. The image-space data can typically be reconstructed by a Fourier transform using the k-space data. Typically, a computing unit 14 of the MRI-PET system 10 is embodied for the reconstruction. The image-space data typically includes at least one magnetic resonance image. The image-space data can be in DICOM format.

Alternatively or additionally, acquisition of the magnetic resonance data can include retrieval of the magnetic resonance data from a memory unit, for example a radiology information system and/or a PACS image archiving system. The magnetic resonance data can be transferred to the memory unit, for example after the performance of the at least one imaging scan. The MRI-PET system 10, in particular a magnetic resonance imaging scanner (MRI) 11 and/or the positron emission tomography scanner (PET) 12 and/or the computing unit 14, can exchange the k-space data and/or image-space data with the memory unit, for example via a network connection.

The MRI data of the at least one imaging scan usually includes at least one slice of the patient P. In other words, the MRI data maps the at least one slice of the patient P. Alternatively or additionally, the MRI data can include a volume of the patient P, wherein typically a plurality of slices of the patient P can be determined from the volume. Conversely, it is in principle conceivable that the plurality of slices is acquired first with the volume of the patient P being determined using the plurality of slices.

The first items of projection data can, for example, include first k-space data. The acquisition of the first items of projection data can include the performance of a first projection scan in the MRI 11 as a result of which the first k-space data can have a radial trajectory. A first projection image can be reconstructed from the first k-space data, in particular by applying a Fourier transform to the first k-space data. The image-space data can include the first projection image. The radial trajectory usually passes through the origin of the k-space. The first projection scan acquires, for example, a first slice of the patient P. The first projection image preferably includes the first slice. In other words, the first slice is depicted in the first projection image. The first slice of the patient P is preferably an axial slice of the patient. The substantially axial direction of the patient is preferably perpendicular to a z-axis of the MRI-PET system 10, in particular the MRI.

The acquisition of the first items of projection data can include the recording of a first slice-selective free-induction decay (FID). The first FID is, for example, acquired with readout encoding by way of the first projection scan. The first items of projection data, in particular the first projection image, preferably include a first projection of a body of the patient P, in particular at the level of patient bench 13, wherein the first projection is preferably spatially accurate. Preferably, the first items of projection data and/or the first projection image are spatially accurate. In this case, the first items of projection data typically have spatial coordinates that are usually in a fixed relationship with a main coordinate system. The acquisition of the first items of projection data in the MRI-PET system 10 can resemble the acquisition of items of projection data in an X-ray based computed tomography scanner.

The second items of projection data can, for example, include second k-space data. The acquisition and further properties of the second items of projection data can substantially correspond to the acquisition and properties of the first items of projection data and therefore, for reasons of clarity, reference is made to the explanations relating to acquisition and properties of the first items of projection data.

The MRI data acquired during the performance of the at least one MRI imaging scan (MRI imaging) 11 typically includes neither the first items of projection data nor the second items of projection data. In other words, during the performance of the at least one imaging scan, the k-space is determined such that the k-space does not contain the first items of projection data and the second items of projection data. In other words, the first items of projection data and the second items of projection data are written to a further k-space, wherein the further k-space, in particular the first items of projection data and/or the second items of projection data, is typically discarded after the adaptation of the at least one sequence parameter of the at least one imaging scan. During the performance of the at least one imaging scan, the k-space is, for example, filled with Cartesian and/or radial and/or spiral trajectories, which form the magnetic resonance data. Therefore, the attenuation map is preferably determined solely based on the magnetic resonance data, in particular without the first items of projection data and the second items of projection data. Alternatively, it is conceivable that the first items of projection data and the second items of projection data are written together with the magnetic resonance data to the same k-space on the basis of which the attenuation map is determined.

The determination of the third items of projection data can include the reconstruction of the first projection image using the first items of projection data and/or the reconstruction of the second projection image using the second items of projection data. For example, the first projection image and second projection image can be merged to form a third projection image, wherein the third items of projection data include the third projection image and/or can be converted into one another. The third projection image can be provided in DICOM format. The merging can include the first slice of the first projection scan and a second slice from a second projection scan being assembled one on top of the other, preferably in a spatially accurate manner. The acquisition of the second items of projection data can include the performance of the second projection scan in the MRI 11.

The merging can include the definition of a point, wherein image information from the first items of projection data, in particular from the first projection image, is used up to the point and image information from the second items of projection data is used up to the point, in particular from the second projection image, is used up to the point. The point can, for example, be a geometric center of the MRI. It is in principle conceivable that, during the merging, the first items of projection data, in particular the first projection image, and/or the second items of projection data, in particular the second projection image, are weighted. The merging can include adding, subtracting and/or masking the first items of projection data and/or the second items of projection data. The merging can take place in dependence on an image quality of the first items of projection data of the patient P and the image quality of the second items of projection data of the patient P. The image quality typically depends on the positioning of a scan region FOV.P1 of the first items of projection data and a scan region FOV.P2 of the second items of projection data relative to a maximum field of view FOV of the MRI-PET system 10.

The determination of the third items of projection data can include the transmission of the first items of projection data and/or the second items of projection data within the MRI-PET system 10, in particular to the computing unit 14. The computing unit 14 and/or the MRI 11 are preferably embodied to merge the first items of projection data and the second items of projection data.

The determination of the mapping P.P can be performed in the computing unit 14 and/or in the MRI 11. The determination of the mapping P.P of the patient P may include the classification and/or segmentation of the third items of projection data, in particular the third projection image. The classification and/or segmentation can include the application of an image algorithm and/or image recognition to the third items of projection data. The mapping P.P of the patient P can be an axial and/or a convex envelope around the patient P. The mapping P.P of the patient can have a one-dimensional intensity value distribution describing a profile of the patient P. The mapping P.P of the patient P can map the anatomy of the patient P. The mapping P.P of the patient P can typically include a location of the patient P, in particular the mounting of the patient P on the patient bench 13. For example, the mapping P.P of the patient P is arranged in the plane perpendicular to the z-axis.

In one example embodiment, the mapping P.P of the patient P includes a maximum axial extent P.A of the patient P. Typically, the maximum extent of the patient P is along an axis on which the arms of the patient P and the body of the patient P lie. The maximum axial extent can be defined by the skin of the patient P and/or the clothing of the patient P.

The adaptation of the at least one sequence parameter of the at least one imaging examination can be performed automatically, for example via the computing unit 14 and/or the MRI 11. The adaptation of the at least one sequence parameter can include the provision of the mapping P.P of the patient P on the display unit 15. For example, a user of the MRI-PET system 10 can adapt the at least one sequence parameter via an input unit. The adaptation of the at least one sequence parameter can include the definition of a further sequence parameter. The at least one sequence parameter can describe an image resolution, a TR time, a TE time, a T1 time, a T2 time, a T2* time, a scan duration, a radio-frequency pulse sequence, a contrast medium injection, a positron emission tracer injection, a readout gradient field, a scan region, a number of partial scans and/or a number of scan regions. The adapted at least one sequence parameter preferably depends on the patient P. In other words, the at least one sequence parameter is preferably defined patient-specifically.

The performance of the at least one imaging scan typically requires the adaptation of the at least one sequence parameter. In other words, the adaptation to the patient P, in particular to the mapping P.P of the patient P, is performed before the performance of the at least one imaging scan. The at least one imaging scan is typically adapted to the mapping P.P of the patient P, in particular to the patient P. Therefore, the attenuation map is typically adapted specifically to the patient P.

The determination of the attenuation map of the patient P using the MRI data typically includes the reconstruction of the image-space data using the k-space data. The determination of the attenuation map can include transmission of the magnetic resonance data from the MRI 11 to the computing unit 14 of the MRI-PET system 10. Alternatively or additionally, the MRI 11 and/or the PET 12 can be embodied to determine the attenuation map. The attenuation map preferably has the same image resolution as the image-space data. Typically, an attenuation value is determined within the attenuation map for each pixel of the image-space data. There is typically an exponential relationship between the attenuation values and the MRI data, in particular the image-space data. There is preferably a 1-1 assignment between the pixels of the MRI data, in particular the image-space data, and the attenuation values of the attenuation map. The attenuation values typically correspond to intensity values. The attenuation map typically includes the distribution of the intensity values, wherein the distribution preferably maps the attenuation behavior of body structures of the patient P. The attenuation behavior of the body structures is usually dependent upon physical properties of the positrons during PET imaging. The attenuation map can be provided in DICOM format.

The provision of the attenuation map can include the transmission of the attenuation map within the MRI-PET system 10 and/or from the MRI 11 to the computing unit 14, and/or from the MRI-PET system 10, in particular from the computing unit 14, to the memory unit, and/or from the computing unit 14 to the PET 12. Alternatively or additionally, the attenuation map can be provided on a display unit 15, for example a monitor, of the MRI-PET system 10.

Figure 2:
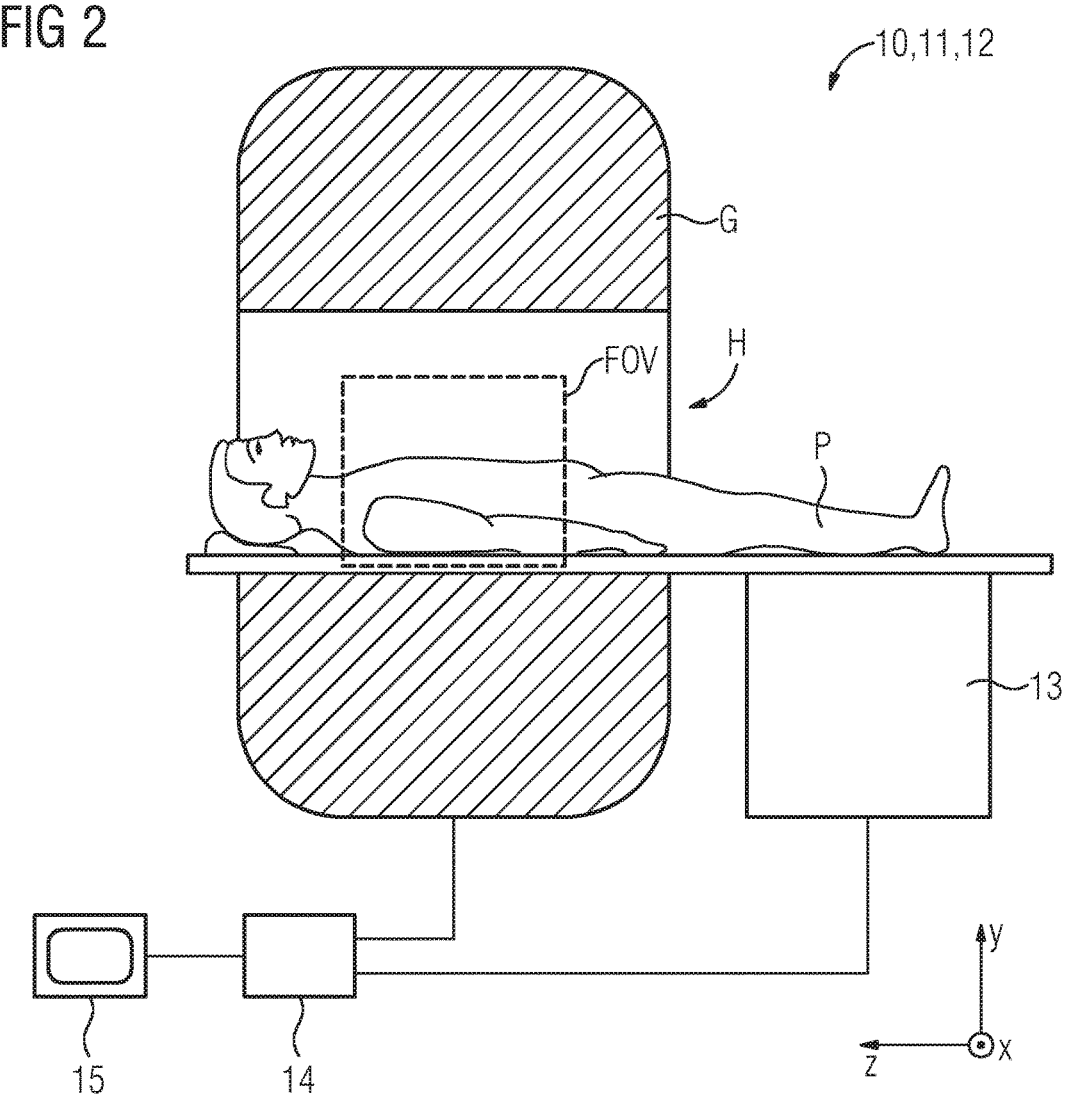

FIG. 2 is a schematic view of a magnetic resonance/positron emission tomography system 10 in a second example embodiment. The MRI-PET system 10 includes the magnetic resonance imaging scanner 11. The MRI 11 is typically embodied for the performance of the at least one imaging scan (MRI imaging). In this example embodiment, the MRI-PET system 10 includes the positron emission tomography scanner 12.

The positron emission data (PET data) is typically acquired during the performance of an imaging scan with PET (PET imaging). The MRI-PET system 10 is typically connected to the MRI 11 and/or the PET 12 in order to exchange the at least one sequence parameter of the imaging scan, to exchange the MRI data and/or to exchange the PET data.

The MRI 11 can be integrated in the PET 12 or the PET 12 can be integrated in the MRI 11. In principle, it is conceivable that the MRI 11 and the PET 12 are arranged within one housing G. In this integrated case, typically the PET 12 imaging scan 12 and the MRI imaging scan is possible without any movement of a patient bench 13 on which the patient P is arranged. In this example embodiment, the MRI 11 and the PET 12 are integrated in the housing G. Alternatively, the MRI 11 and the PET 12 can each have a separate housing. In this case, the patient bench 13 is typically moved between the two housings for the PET 12 imaging scan and the MRI 11 imaging scan.

The housing G typically includes a tunnel-shaped cavity H. The tunnel-shaped cavity H, in which typically the patient P is arranged on the patient bench 13, usually has a diameter in the range of 60 and 70 cm. For example, the maximum field of view FOV of the MRI-PET system 10 has an axial extent which is approximately 10 cm shorter than the diameter of the tunnel-shaped cavity H. Relative to the tunnel-shaped cavity, the maximum field of view FOV is typically arranged centrally for MRI imaging and/or for PET imaging.

The MRI-PET system 10 includes a computing unit 14 and a display unit 15.

Figure 3:
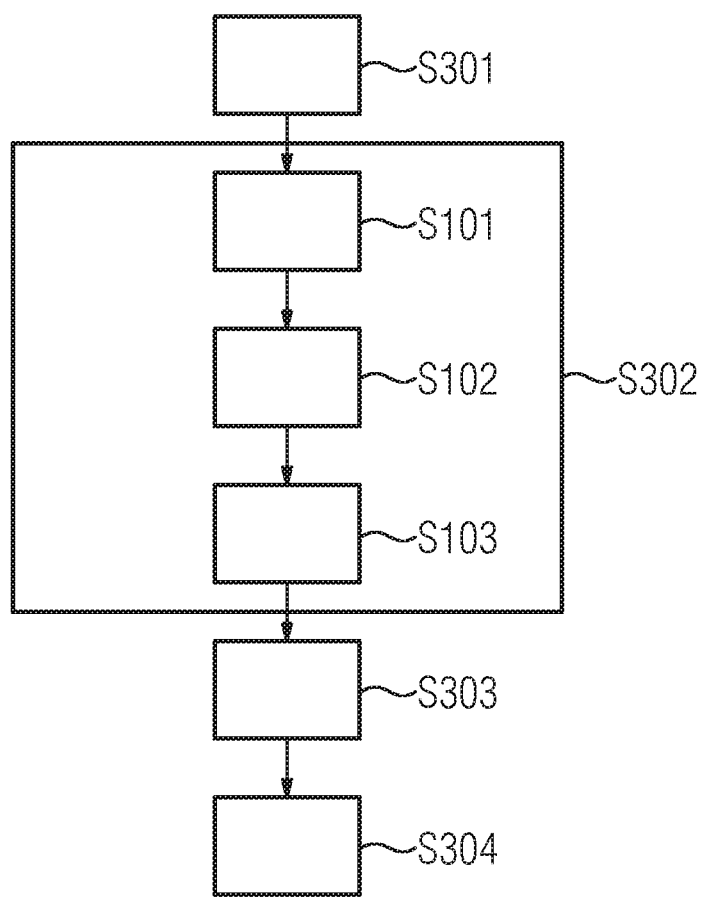

FIG. 3 is a flow diagram of a method for providing corrected PET data of the patient acquired with combined magnetic resonance/positron emission tomography imaging in a magnetic resonance/positron emission tomography system in a third example embodiment.

Method step S301 characterizes the acquisition of the PET data of the patient in the magnetic resonance/positron emission tomography system 10.

Method step S302 characterizes the provision of the attenuation map in accordance with method steps S101 to S103.

Method step S303 characterizes the correction of the PET data of the patient using the attenuation map.

Method step S304 characterizes the provision of the corrected PET data of the patient.

The acquisition of the PET data typically includes the injection of a positron emission tracer, which in particular emits positrons. One positron out of these positrons is typically propagated on a path until it meets an electron, wherein two annihilation photons are generated. The PET 11 typically includes a photon detector to acquire the annihilation photons, wherein the PET data is generated. Preferably, the PET 11 can use the PET data to reconstruct the location within the MRI-PET system 10 at which the meeting of the electron and the positron has occurred. This location typically corresponds to the origin of the positron emission. In other words, the PET data preferably includes the distribution of the locations at which the positrons collide with the electrons.

Since the annihilation photons are typically attenuated on their way to the photon detector, for this reason the attenuation map is used for the provision of the corrected PET data. The use of the attenuation map can include the scaling, interpolation, extrapolation and/or displacement of the PET data. As a result of the correction of the PET data by way of the attenuation map, preferably spatially accurate positron emission data is determined. In other words, the corrected PET data preferably includes a spatially accurate distribution of tracer activity, in particular within the patient P, wherein the tracer activity can be described approximately by the origin of the positron emission. The PET data can be corrected in the MRI-PET system 10, in particular in the computing unit 14, in the MRI 11 and/or in the PET 12. The corrected PET data can, for example, be used by a physician for diagnosis if the corrected PET data is provided on the display unit 15.

Figure 4:
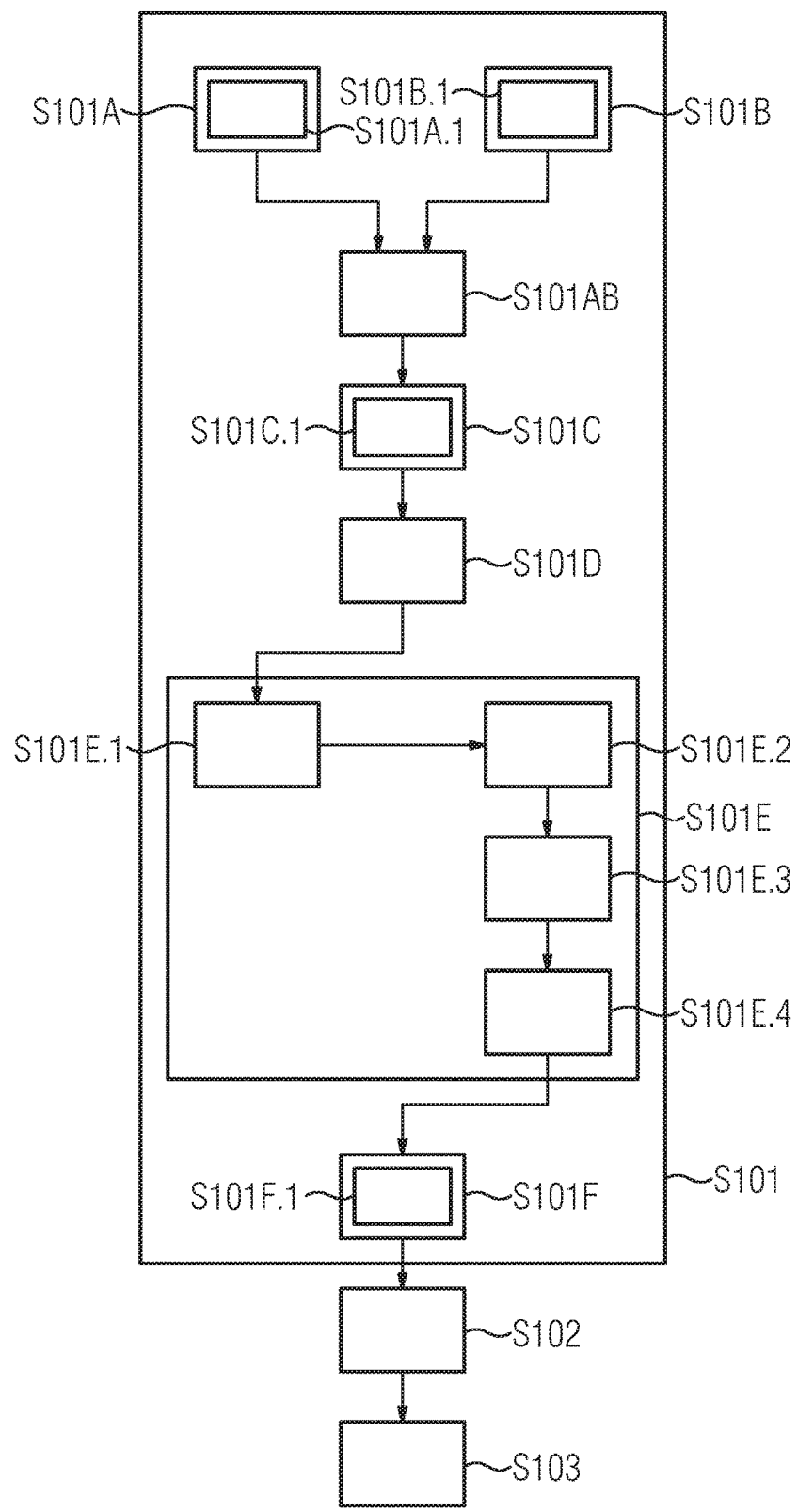

FIG. 4 is a flow diagram of a method for providing an attenuation map of a patient P in a fourth example embodiment.

Method step S101A.1 and method step S101B.1 characterize the fact that a scan region FOV.P1 of the first items of projection data and a scan region FOV.P2 of the second items of projection data are arranged offset along a longitudinal axis P.L of the patient P. In this case, the first items of projection data and the second items of projection data are arranged offset along the longitudinal axis P.L. The longitudinal axis P.L of the patient P is preferably parallel to a z-axis of the MRI-PET system 10. The substantially axial direction of the patient P is preferably in the x-y plane of the MRI-PET system 10.

Method step S101AB characterizes the fact that the first items of projection data of the patient P and/or the second items of projection data of the patient P are displaced along the longitudinal axis P.L of the patient P such that the first items of projection data and the second items of projection data along the longitudinal axis P.L have the same longitudinal position as a result of which the third items of projection data of the patient P have the same longitudinal position. In particular if the scan region FOV.P1 of the first items of projection data and the scan region FOV.P2 of the second items of projection data are displaced along the longitudinal axis P.L of the patient P, in particular are arranged offset, the displacement of the first items of projection data of the patient P and/or the second items of projection data of the patient P causes the third items of projection data to be depicted preferably in one plane. The displacement can include the interpolation, extrapolation and/or weighting of the first, in particular spatially accurate, items of projection data and/or the second, in particular spatially accurate, items of projection data.

Method step S101C.1 characterizes the fact that, during the determination of the third items of projection data, the first items of projection data of the patient P and the second items of projection data of the patient P are merged such that the third items of projection data have an axial extent A.P3, which is greater than an axial extent A.P1 of the first items of projection data of the patient P or than an axial extent A.P2 of the second items of projection data of the patient P. The axial extent A.P1 of the first items of projection data of the patient P and/or an axial extent A.P2 of the second items of projection data of the patient P can be less than 100%, 80%, 60% and/or 40% of a maximum axial extent of the maximum field of view FOV. In particular, if the image quality of the first items of projection data and/or the image quality of the second items of projection data at the edges of the scan region FOV.P1 of the first items of projection data and the scan region FOV.P2 of the second items of projection data varies due to the anatomy and/or location of the patient, the axial extent A.P3 can preferably nevertheless be greater than a maximum axial extent P.A of the patient P.

Method step S101E.1 characterizes the fact that the adaptation of the at least one sequence parameter includes a definition of a readout gradient field of the at least one imaging scan in accordance with the mapping P.P of the patient P such that, at a predetermined location within a scan region FOV.M of the at least one imaging scan, distortion caused by non-linearity of the readout gradient field and distortion caused by B0 field inhomogeneity substantially cancel each other out. This typically enhances the image quality of the MRI data. The definition of the readout gradient field can include the definition of an amplitude and/or a direction of the readout gradient field.

Method step S101E.2 characterizes the fact that the adaptation of the at least one sequence parameter includes the definition of a substantially axial extent A.M of a scan region FOV.M of the at least one imaging scan in accordance with the mapping P.P of the patient P. The axial extent A.M of the scan region FOV.M is preferably the same as the maximum axial extent P.A of the patient P in order to reduce aliasing in the MRI data. Particularly advantageously, the axial extent A.M of the scan region FOV.M is greater than the maximum axial extent P.A of the patient P, as a result of which aliasing in the MRI data can preferably be completely prevented, and smaller than the maximum axial extent of the maximum field of view FOV, as a result of which typically a scan duration of the at least one imaging scan is reduced.

Method step S101E.3 characterizes the fact that the adaptation of the at least one sequence parameter includes the division of the at least one imaging scan into a plurality of partial scans in accordance with the mapping P.P of the patient P. Readout gradient fields of the plurality of partial scans are typically adapted separately, in particular optimized, for each partial scan. Distortion caused, for example, due to the B0 field inhomogeneities, can typically be reduced separately in each partial scan, in particular by way of the adaptation of the readout gradient field. In each of the partial scans, typically items of scan data are generated, which can typically be combined to form the MRI data. In other words, the MRI data usually includes the items of scan data of the plurality of partial scans.

Method step S101E.4 characterizes the fact that a plurality of scan regions FOV.M1, FOV.M2 is assigned to the plurality of partial scans with the plurality of scan regions FOV.M1, FOV.M2 being arranged offset along a longitudinal axis P.L of the patient P. During the performance of the plurality of partial scans in the plurality of scan regions FOV.M1, FOV.M2, typically saturation effects can occur and can result in signal extinction in the items of scan data from the plurality of partial scans, in particular in the MRI data. Since the saturation effects typically depend on the position of the plurality of scan regions FOV.M1, FOV.M2 relative to one another, a temporal offset between the plurality of partial scans may be necessary for the preferable reduction of signal extinction. The offset of the plurality of scan regions FOV.M1, FOV.M2 along the longitudinal axis P.L of the patient P typically enables the reduction of signal extinction and/or the scan duration of the plurality of partial scans.

Method step S101F.1 characterizes the fact that the plurality of partial scans includes a first partial scan and a second partial scan, wherein, during the performance of the first partial scan of the at least one imaging scan, first items of scan data are acquired, wherein, during the performance of the second partial scan of the at least one imaging scan, second items of scan data are acquired and wherein the first items of scan data and/or the second items of scan data are displaced along the longitudinal axis P.L of the patient P such that the first items of scan data and the second items of scan data along the longitudinal axis P.L have the same longitudinal position as a result of which the magnetic resonance data have the same longitudinal position. The first partial scan is usually performed in the scan region FOV.M1 of the first items of scan data. The second partial scan is typically performed in the scan region FOV.M2 of the second items of scan data. The scan region FOV.M1 of the first items of scan data and the scan region FOV.M2 of the second items of scan data typically have different longitudinal positions, while, after displacement, the MRI data has the same longitudinal axis.

Figure 5:
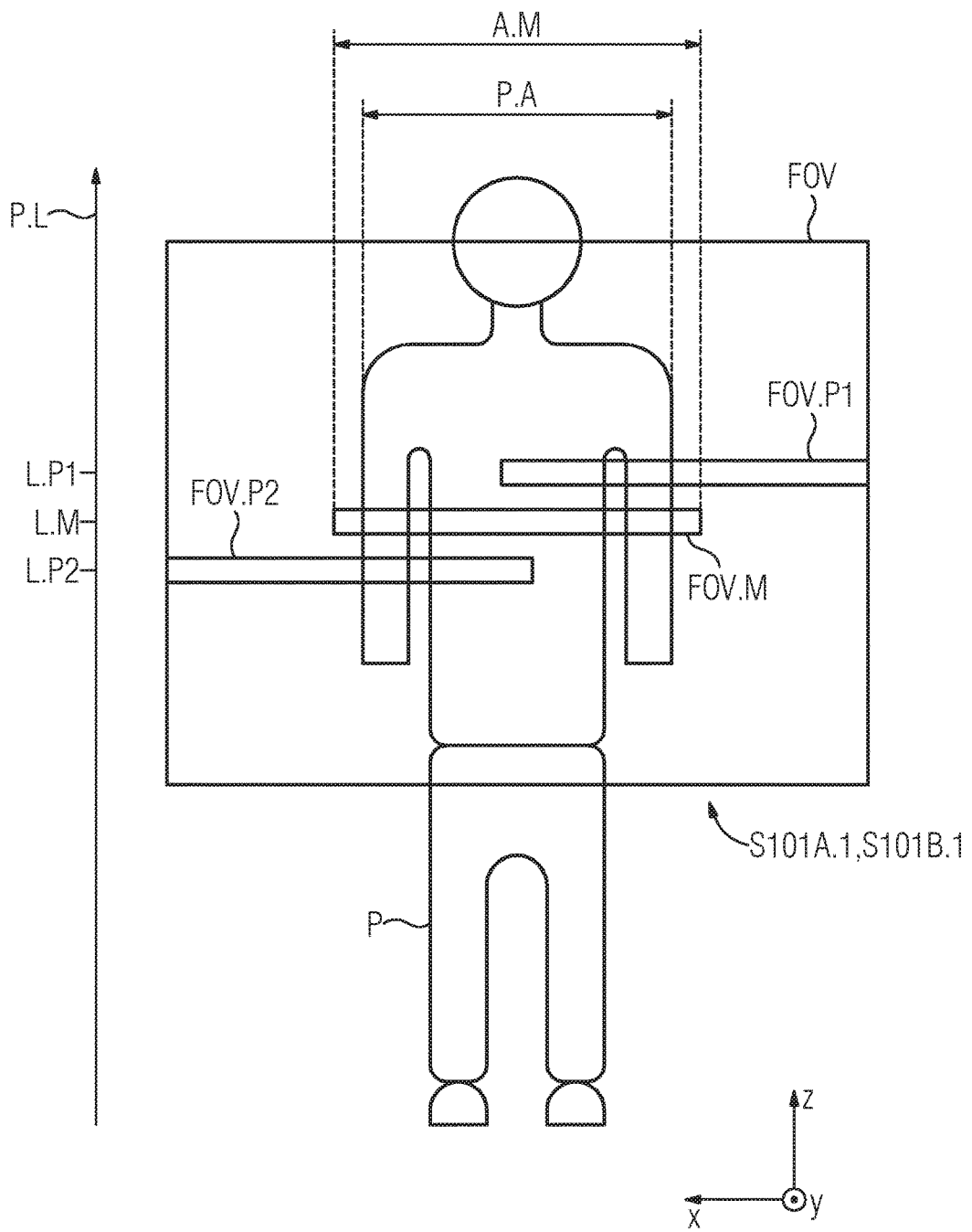

FIG. 5 shows a possible positioning of the scan region FOV.P1 of the first items of projection data, the scan region FOV.P2 of the second items of projection data and the scan region FOV.M of the at least one imaging scan relative to one another.

The patient P is depicted schematically in a front view. The longitudinal axis P.L of the patient P is aligned parallel to the z-axis. The maximum field of view FOV includes the upper body and arms of the patient P.

In this example embodiment, it is depicted according to method step S101A.1 and method step S101B.1 that the scan region FOV.P1 of the first items of projection data and the scan region FOV.P2 of the second items of projection data are arranged offset along the longitudinal axis P.L of the patient P. The first items of projection data, in particular the scan region FOV.P1 of the first items of projection data, has a longitudinal position L.P1 that differs from the longitudinal position L.P2 of the scan region FOV.P2 of the second items of projection data and from the longitudinal position L.M of the scan region FOV.M of the at least one imaging scan.

The scan region FOV.M of the at least one imaging scan is arranged between the scan region FOV.P1 of the first items of projection data and the scan region FOV.P2 of the second items of projection data. The scan region FOV.M of the at least one imaging scan can in principle include the longitudinal position L.P1 of the scan region FOV.P1 of the first items of projection data, the longitudinal position L.P2 of the scan region FOV.P2 of the second items of projection data, the longitudinal position L.P3 of the third items of projection data, and/or any further longitudinal position of the longitudinal axis P.L of the patient P.

The respective scan regions FOV.M, FOV.M1, FOV.M2, FOV.P1, FOV.P2 typically include in particular axial slices of the patient P. In this case, the angle between the respective scan regions FOV.M, FOV.M1, FOV.M2, FOV.P1, FOV.P2 relative to the longitudinal axis P.L of the patient P is preferably 90°. In principle, it is conceivable that the angle is greater or smaller than 90°. In other words, the respective scan regions FOV.M, FOV.M1, FOV.M2, FOV.P1, FOV.P2 can be aligned non-parallel to the x-y plane of the MRI-PET system 10.

According to the method step S101E.2, the scan region FOV.M of the at least one imaging scan is defined such that the substantially axial extent A.M of the scan region FOV.M of the at least one imaging scan is greater than the maximum axial extent P.A of the patient P.

Figure 6:
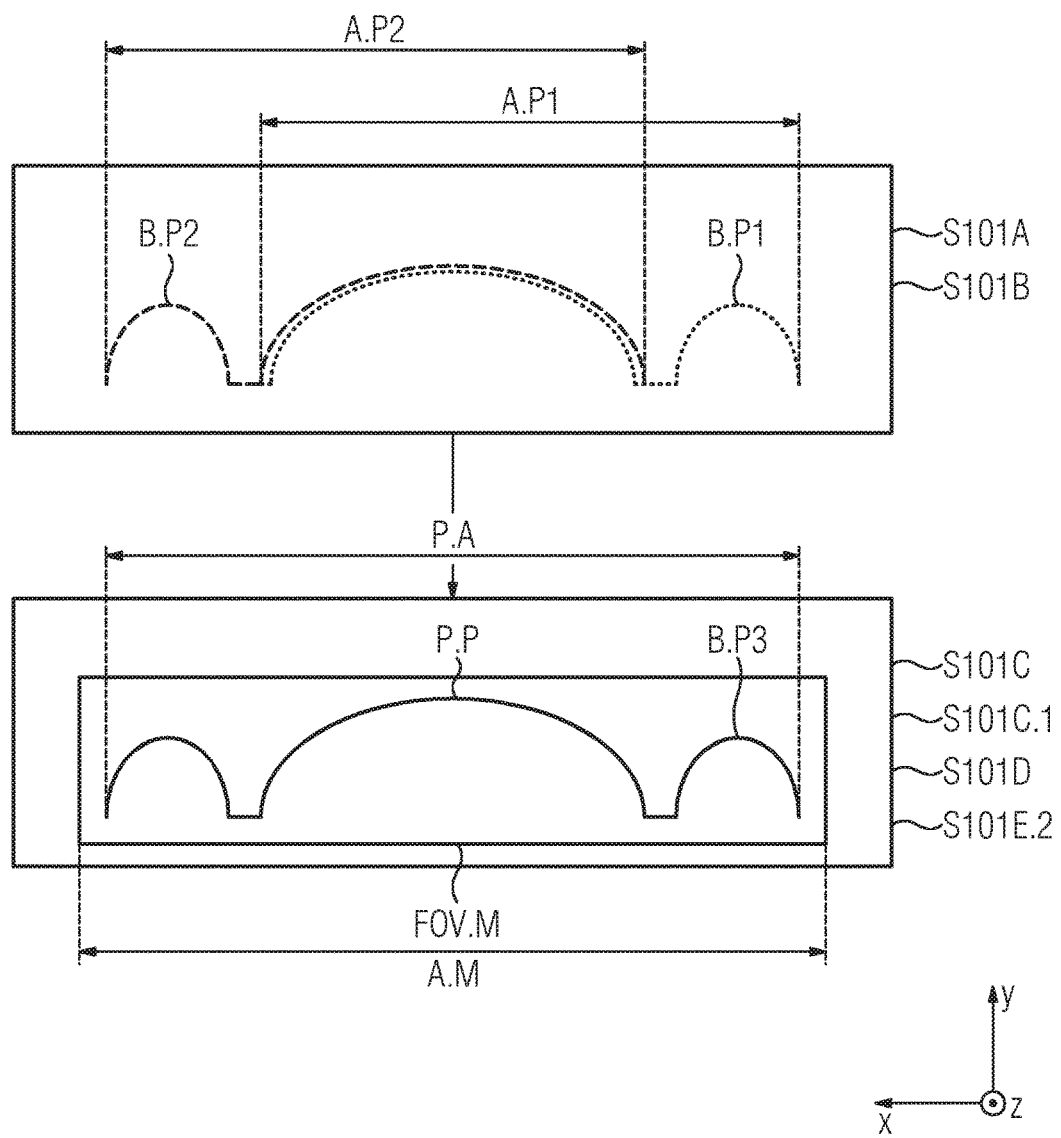

FIG. 6 shows a sequence diagram with example data illustrating how a possible third projection image B.P3 can be formed by merging a possible first projection image B.P1 and a possible second projection image B.P2. FIG. 6 also shows the scan region FOV.M of the at least one imaging scan. FIG. 6 shows the mapping P.P of the patient P at a longitudinal position of the patient at the height of the upper body with the arms of the patient, for example at the longitudinal position L.P1 of the scan region FOV.P1 of the first items of projection data.

In this example embodiment, the first items of projection data, in particular the first projection image B.P1, the second items of projection data, in particular the second projection image B.P2, and the third items of projection data, in particular the third projection image B.P3, are spatially accurate. For reasons of clarity, in FIG. 6, the first projection image B.P1, as a dotted line, the second projection image B.P2, as a dashed line and/or the third projection image B.P3, as a solid line are combined within several overviews.

The first items of projection data, in particular the first projection image B.P1, and the second items of projection data, in particular the second projection image B.P2, only depict the patient P partially in the substantially axial direction of the patient P at the longitudinal position shown in FIG. 6. The axial extent A.P1 of the first items of projection data and the axial extent A.P2 of the second items of projection data are smaller than the maximum axial extent P.A of the patient P, in particular at the longitudinal position shown in FIG. 6. The third items of projection data, in particular the third projection image B.P3, depict the patient P completely in the substantially axial direction of the patient P. In this example embodiment, the scan region FOV.M of the at least one imaging scan is greater in the substantially axial direction than the maximum axial extent P.A of the patient P.

FIG. 7 shows possible partial scan regions FOV.M1, FOV.M2, FOV.N of the plurality of partial scans.

FIG. 7 shows in accordance with method step S101E.3 that the adaptation of the at least one sequence parameter includes the division of the at least one imaging scan into a plurality of partial scans in accordance with the mapping P.P of the patient P.

FIG. 7 shows in accordance with method step S101E.4 that a plurality of scan regions FOV.M1, FOV.M2 are assigned to the plurality of partial scans and wherein the plurality of scan regions FOV.M1, FOV.M2 are arranged offset along a longitudinal axis P.L of the patient P.

The partial scans can each be adapted for opposite sides of the plurality of partial scan regions FOV.M1, FOV.M2, FOV.N. In other words, the readout gradient fields of the plurality of partial scans can be defined for a first body half and for a second body half independently of one another. The first body half can, for example, include a right arm of the patient P and the second body half can, for example, include a left arm of the patient P. The image quality of the MRI data is typically better if the readout gradient fields are each adapted for the first body half and the second body half independently of one another.

In FIG. 7, partial scan regions FOV.M1, FOV.M2, FOV.N of the partial scans of the first body half are depicted as dotted and partial scan regions of the partial scans of the second body half are depicted as dashed. In each case, a partial scan of a dotted partial scan region and a partial scan of a dashed partial scan region are characterized as belonging together by a parenthesis. In accordance with method step S101F.1, the first items of scan data, for example the dotted partial scan region, and/or the second items of scan data for example the dashed partial scan region are displaced along the longitudinal axis P.L of the patient P such that the first items of scan data and the second items of scan data along the longitudinal axis P.L have the same longitudinal position as a result of which the magnetic resonance data has the same longitudinal position. Prior to adding to the MRI data, the first items of scan data and/or the second items of scan data can be weighted and/or masked.

Particularly advantageously, the maximum axial extent P.A of the patient can be determined in accordance with the mapping P.P of the patient P for several longitudinal positions of the patient P. In this case, the at least one imaging scan is adapted to the anatomy and/or location of the patient P as a result of which preferably the scan duration is preferably optimized.

Although the invention was described in more detail by the preferred example embodiments, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing an attenuation map of a patient, suitable for correcting PET data of the patient acquired with combined magnetic resonance/positron emission tomography imaging in a magnetic resonance/positron emission tomography system, the method comprising:
   acquiring magnetic resonance data with at least one imaging scan in the magnetic resonance/positron emission tomography system;
   determining the attenuation map of the patient using the magnetic resonance data acquired; and
   providing the attenuation map of the patient for correcting the PET data of the patient acquired with the combined magnetic resonance/positron emission tomography imaging,
   wherein the acquiring of the magnetic resonance data includes:
   acquiring first items of projection data of the patient in a substantially axial direction of the patient,
   acquiring second items of projection data of the patient in the substantially axial direction of the patient,
   determining third items of projection data by merging the first items of projection data of the patient and the second items of projection data of the patient acquired,
   determining mapping of the patient using the third items of projection data determined,
   adapting at least one sequence parameter of the at least one imaging scan in accordance with the mapping of the patient, and
   performing the at least one imaging scan to acquire the magnetic resonance data.

2. The method of claim 1, wherein the adapting of the at least one sequence parameter includes:
   defining a readout gradient field of the at least one imaging scan in accordance with the mapping of the patient such that, at a location within a scan region of the at least one imaging scan, distortion caused by non-linearity of the readout gradient field and distortion caused by B0 field inhomogeneity are substantially cancelled out.

3. The method of claim 2, wherein the mapping of the patient includes a maximum axial extent of the patient.

4. The method of claim 2, wherein the adapting of the at least one sequence parameter includes:
   defining a substantially axial extent of a scan region of the at least one imaging scan in accordance with the mapping of the patient.

5. The method as of claim 4, wherein the adapting of the at least one sequence parameter includes division of the at least one imaging scan into a plurality of partial scans in accordance with the mapping of the patient.

6. The method of claim 2, wherein a scan region of the first items of projection data and a scan region of the second items of projection data are arranged offset along a longitudinal axis of the patient.

7. The method of claim 6, wherein at least one of the first items of projection data of the patient and the second items of projection data of the patient are displaced along the longitudinal axis of the patient such that the at least one of the first items of projection data and the second items of projection data along the longitudinal axis have a same longitudinal position, resulting in the third items of projection data of the patient having a same longitudinal position.

8. The method of claim 1, wherein the mapping of the patient includes a maximum axial extent of the patient.

9. The method of claim 1, wherein the adapting of the at least one sequence parameter includes:
   defining a substantially axial extent of a scan region of the at least one imaging scan in accordance with the mapping of the patient.

10. The method as of claim 1, wherein the adapting of the at least one sequence parameter includes division of the at least one imaging scan into a plurality of partial scans in accordance with the mapping of the patient.

11. The method of claim 10, wherein a plurality of scan regions are assigned to the plurality of partial scans and wherein the plurality of scan regions are arranged offset along a longitudinal axis of the patient.

12. The method of claim 11, wherein the plurality of partial scans includes a first partial scan and a second partial scan, wherein, during performance of the first partial scan of the at least one imaging scan, first items of scan data are acquired, wherein, during performance of the second partial scan of the at least one imaging scan, second items of scan data are acquired and wherein at least one of the first items of scan data and the second items of scan data are displaced along the longitudinal axis of the patient such that the at least one of the first items of scan data and the second items of scan data have a same longitudinal position along the longitudinal axis, resulting in the magnetic resonance data having a same longitudinal position.

13. The method of claim 1, wherein a scan region of the first items of projection data and a scan region of the second items of projection data are arranged offset along a longitudinal axis of the patient.

14. The method of claim 13, wherein at least one of the first items of projection data of the patient and the second items of projection data of the patient are displaced along the longitudinal axis of the patient such that the at least one of the first items of projection data and the second items of projection data along the longitudinal axis have a same longitudinal position, resulting in the third items of projection data of the patient having a same longitudinal position.

15. The method of claim 1, wherein, during the determining of the third items of projection data, the first items of projection data of the patient and the second items of projection data of the patient are merged such that the third items of projection data have an axial extent, relatively greater than an axial extent of the first items of projection data of the patient or an axial extent of the second items of projection data of the patient.

16. A method for providing corrected PET data of the patient acquired with the combined magnetic resonance/positron emission tomography imaging in the magnetic resonance/positron emission tomography system, the method comprising:
   acquiring the PET data of the patient in the combined magnetic resonance/positron emission tomography system,
   providing the attenuation map according to the method of claim 1,
   correcting the PET data of the patient using the attenuation map and providing the corrected PET data of the patient.

17. A magnetic resonance/positron emission tomography system, comprising:
   a magnetic resonance imaging scanner, embodied to at least
      acquire magnetic resonance data with at least one imaging scan in the magnetic resonance/positron emission tomography system;
      determine an attenuation map of a patient using the magnetic resonance data acquired; and
      provide the attenuation map of the patient for correcting PET data of the patient acquired with the magnetic resonance/positron emission tomography system,
   wherein acquiring of the magnetic resonance data includes the magnetic resonance imaging scanner being embodied to at least:
      acquire first items of projection data of the patient in a substantially axial direction of the patient,
      acquire second items of projection data of the patient in the substantially axial direction of the patient,
      determine third items of projection data by merging the first items of projection data of the patient and the second items of projection data of the patient acquired,
      determine mapping of the patient using the third items of projection data determined,
      adapt at least one sequence parameter of the at least one imaging scan in accordance with the mapping of the patient, and
      perform the at least one imaging scan to acquire the magnetic resonance data.

18. The magnetic resonance/positron emission tomography system of claim 17, further comprising:
   a positron emission tomography scanner.

19. A non-transitory computer readable medium including program code segments, loadable into a computing unit of a magnetic resonance/positron emission tomography system, wherein when the program code segments are executed on the computing unit, a method is carried out for providing an attenuation map of a patient, suitable for correcting PET data of the patient acquired with combined magnetic resonance/positron emission tomography imaging in the magnetic resonance positron emission tomography system, the method comprising:
   acquiring magnetic resonance data with at least one imaging scan in the magnetic resonance/positron emission tomography system;
   determining the attenuation map of the patient using the magnetic resonance data acquired; and
   providing the attenuation map of the patient for correcting the PET data of the patient acquired with the combined magnetic resonance/positron emission tomography imaging,
   wherein the acquiring of the magnetic resonance data includes:
   acquiring first items of projection data of the patient in a substantially axial direction of the patient,
   acquiring second items of projection data of the patient in the substantially axial direction of the patient,
   determining third items of projection data by merging the first items of projection data of the patient and the second items of projection data of the patient acquired,
   determining mapping of the patient using the third items of projection data determined,
   adapting at least one sequence parameter of the at least one imaging scan in accordance with the mapping of the patient, and
   performing the at least one imaging scan to acquire the magnetic resonance data.

20. The non-transitory computer readable medium of claim 19, wherein the adapting of the at least one sequence parameter includes:
   defining a readout gradient field of the at least one imaging scan in accordance with the mapping of the patient such that, at a location within a scan region of the at least one imaging scan, distortion caused by non-linearity of the readout gradient field and distortion caused by B0 field inhomogeneity are substantially cancelled out.

* * * * *